United States Patent [19]

Knorr et al.

[11] 4,433,153

[45] Feb. 21, 1984

[54] PROCESS FOR THE MANUFACTURE OF 2,6-DICHLOROBENZOXAZOLE AND 2,6-DICHLOROBENZTHIAZOLE

[75] Inventors: Harald Knorr, Gersthofen; Reinhard Handte, Hofheim am Taunus; Lothar Willms, Unkel; Thomas Tammer, Hofheim am Taunus, all of Fed. Rep. of Germany

[73] Assignee: Hoechst Aktiengesellschaft, Fed. Rep. of Germany

[21] Appl. No.: 281,215

[22] Filed: Jul. 7, 1981

[51] Int. Cl.³ ................. C07D 263/58; C07D 277/68
[52] U.S. Cl. ..................................... 548/152; 548/217
[58] Field of Search ............................. 548/152, 217

[56] References Cited

U.S. PATENT DOCUMENTS

| | | | |
|---|---|---|---|
| 1,878,699 | 9/1932 | Hentrich et al. | 548/152 |
| 3,108,104 | 10/1963 | Seefelder et al. | 548/217 |
| 3,284,294 | 11/1966 | Sasse et al. | 548/217 |

FOREIGN PATENT DOCUMENTS

| | | | |
|---|---|---|---|
| 1670453 | 2/1971 | Fed. Rep. of Germany. | |
| 2800462 | 7/1978 | Fed. Rep. of Germany. | |
| 913910 | 12/1962 | United Kingdom | 548/152 |

*Primary Examiner*—Paul M. Coughlan, Jr.
*Assistant Examiner*—David B. Springer
*Attorney, Agent, or Firm*—Connolly and Hutz

[57] ABSTRACT

A process for the manufacture of 2,6-dichlorobenzoxazole and 2,6-dichlorobenzthiazole by chlorinating K+ or Na+ salts of 6-chloro-2-mercaptobenzoxazole or of 6-chloro-2-mercaptobenzthiazole in halogenated hydrocarbons as suspending agents.

7 Claims, No Drawings

PROCESS FOR THE MANUFACTURE OF 2,6-DICHLOROBENZOXAZOLE AND 2,6-DICHLOROBENZTHIAZOLE

It is known that 2-chlorobenzthiazoles and 2-chlorobenzoxazoles can be prepared from the corresponding 2-mercaptobenzazoles by direct chlorination (German Offenlegungsschrift No. 1,670,453, and J. Org. Chem. 23, 1,500 (1958)). In this process, the reaction is carried out, in the case of the thiazole, at elevated temperatures and in the presence of catalytically active quantities of N-substituted carboxylic acid amides, such as, for example, dimethylformamide, and 2-chlorobenzthiazole is obtained in a yield of pure material of 87% of theory.

The oxazole is also prepared by carrying out the reaction in an inert solvent, but at a low temperature and without the addition of a catalyst; the yield of 2-chlorobenzoxazole is 82% of theory. If it is now desired to synthesize 2,6-dichlorobenzthiazole and 2,6-dichlorobenzoxazole, which are valuable intermediate products, for example for the manufacture of active compounds for plant protection (German Offenlegungsschrift No. 2,640,730), in the same manner, but using 6-chloro-2-mercaptobenzthiazole and 6-chloro-2-mercaptobenzoxazole as the starting materials, it has to be stated that, in this case, it is only possible to achieve considerably lower yields and that a large quantity of undistillable residues is formed.

The present invention is therefore based on the object of improving the yields in the preparation of 2,6-dichlorobenzthiazole and 2,6-dichlorobenzoxazole and of reducing the formation of by-products which cannot be utilized further.

It has been found that this is possible if the potassium or sodium salts of 6-chloro-2-mercaptobenzthiazole are chlorinated instead of the free compound and if these salts are suspended, for this reaction, in special inert solvents.

The invention relates, therefore, to a process for the manufacture of 2,6-dichlorobenzthiazole and 2,6-dichlorobenzoxazole of the formula

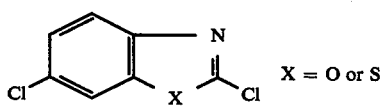

X = O or S which comprises subjecting the potassium or sodium salts of 6-chloro-2-mercaptobenzoxazole or 6-chloro-2-mercaptobenzthiazole to chlorination in the presence of a halogenated aliphatic or aromatic hydrocarbon, as a suspending agent.

Yields of 90% or more of the desired process products are obtained by the procedure according to the invention. The quantities of residue are correspondingly low.

From many points of view it could not be foreseen that the reaction would proceed smoothly. Thus, it is surprising that the reaction takes place at all, since the alkali metal salts of the free mercapto compounds are virtually insoluble in the halogenated hydrocarbons used. Secondly, it was known that only the disulfides are formed if benzthiazole and benzoxazole mercaptides are chlorinated in solution (German Offenlegungsschrift No. 2,800,462).

The process according to the invention also makes it possible to use, as starting materials, without having to accept an appreciable reduction in yield thereby, crude alkali metal 2-mercaptides of 6-chlorobenzthiazole or 6-chlorobenzoxazole, which are available as intermediate products.

The chlorination is carried out in the temperature range between −20° and +150° C. Somewhat higher temperatures are required for the chlorination of the thiazole (>20° C., preferably 80°–100°) than for the chlorination of the oxazole, which is carried out at the temperature which is set up spontaneously, namely between −10° and 100° C., preferably between 20° and 60° C. In the chlorination of the thiazole it is advantageous to follow a procedure in which part of the quantity of chlorine required is passed in at temperatures from 20° to 80° C., until the sulfenyl chloride has been formed, after which the temperatures are increased and chlorination is continued. It is also possible to pass in all the chlorine at the higher temperature. In the case of the oxazole, the chlorination of the sulfenyl chloride which is formed as an intermediate does not require elevated temperatures.

The quantity of chlorine required is approx. 2.3 to 3 moles per mole of alkali metal mercaptide employed, if the chlorine is passed into the reaction mixture at atmospheric pressure. If the reaction is carried out in a closed system, that is to say excluding chlorine losses as far as possible, it is possible to reduce the quantity of chlorine to 2 to approx. 2.3 moles.

The solvents used are halogenated hydrocarbons, such as, for example, carbon tetrachloride, tetrachloroethane or chlorinated benzenes, but chiefly chlorobenzene and o-dichlorobenzene and particularly the last of these. In general, the quantities of solvent are such that the suspension formed can still be stirred. However, it is also possible to use less solvent and then to pass chlorine into the suspension under pressure in a closed system.

If desired, catalytic quantities of an N-substituted carboxylic acid amide, for example dimethylformamide, can be added in order to accelerate the reaction.

When the reaction is complete, the sulfur dichloride formed in the reaction is removed by distillation, if appropriate also as a mixture with the solvent, it being possible to re-use the latter.

The alkali metal chloride produced in the chlorination can be removed by filtration or, in the case of the chlorination of thiazole, extracted with water after previously removing the sulfur dichloride.

The alkali metal mercaptides of 6-chloro-2-mercaptobenzoxazole and 6-chloro-2-mercaptobenzthiazole required as starting materials are accessible, for example, by the process described in German Patent Application No. P 30 08 22.5, or can be prepared by reacting 5-chloro-2-aminophenol with alkali metal xanthates.

The process according to the invention is carried out, for example, by suspending the mercaptide (particularly the potassium salt, in the case of 6-chloro-2-mercaptobenzoxazole) in the solvent and passing in 1.0 to 1.05 moles of chlorine per mole of mercaptide, initially at room temperature, if appropriate with cooling and, if appropriate, in the presence of catalytically active quantities of dimethylformamide (0.1 to 5% by weight, relative to the mercaptide). The mixture is then heated, in the case of the thiazole, to 80° to 100° C. and a further 1.3 to 2.0 moles of chlorine are passed in at this temperature; in the case of the oxazole, the further chlorine is also added at room temperature. The sulfur dichloride which has been formed is then distilled off, the alkali metal chlorides are removed by filtration or by extraction with water and, finally, the volatile constituents (solvent) are removed by distillation under normal pressure. The 2,6-dichlorobenzazoles are then obtained in a very pure condition by distillation in vacuo. It is possible to dispense with further purification of the reaction products.

The following examples are intended to illustrate the invention in greater detail.

EXAMPLE 1

240 g (1 mole) of potassium 2-mercapto-6-chlorobenzthiazole are suspended in 800 ml of tetrachloroethane and 3.5 g of dimethylformamide are added. 1.0 mole of chlorine is passed in at room temperature and 1.4 moles of chlorine are passed in at 85° to 90° C. The sulfur dichloride is then distilled off, together with a little tetrachloroethane, and the potassium chloride is filtered off and rinsed with 200 ml of tetrachloroethane. After the tetrachloroethane has been removed by distillation under normal pressure, 192.1 g of 2,6-dichlorobenzthiazole (99.6% pure according to gas chromatography), corresponding to a yield of pure material of 93.8% of theory, are obtained by vacuum distillation (under 1.3 mbars). Melting point 96° C.

EXAMPLE 2

The reaction is carried out as described in Example 1. However, 3.0 moles of chlorine are passed in. The solvent used is chlorobenzene.

Yield: 191.1 g of 2,6-dichlorobenzthiazole (99.9% pure according to gas chromatography), corresponding to a yield of pure material of 93.7% of theory. Melting point 96° C.

EXAMPLE 3

240 g (1 mole) of 98% strength potassium 2-mercapto-6-chlorobenzthiazole are suspended in 800 ml of chlorobenzene. 3.5 g of dimethylformamide are added and 1 mole of chlorine is passed in initially at room temperature, followed by a further 2 moles of chlorine at 85° to 90° C. The sulfur dichloride which has been formed is then distilled off, together with some chlorobenzene (150.9 g), and 200 ml of water are added at approx. 60° C. The aqueous phase is drained off, after which the solvent is distilled off from the organic phase under normal pressure. The residue is distilled in vacuo, under 1.3 mbars, 187.4 g of 2,6-dichlorobenzthiazole (98% pure according to gas chromatography) being produced, corresponding to a yield of pure material of 92.0% of theory. Melting point 95° C.

EXAMPLE 4

The reaction is carried out as in Example 1, but without the addition of dimethylformamide, and 190.6 g (93.4% of theory) of 2,6-dichlorobenzthiazole are obtained.

EXAMPLE 5

223.5 g (1 mole) of potassium 6-chloro-2-mercaptobenzoxazole are suspended in 500 ml of chlorobenzene and 180 g (2.5 moles) of chlorine gas are added in the course of 3 hours at a temperature of approx. 25° C. Stirring is continued for 12 hours at room temperature and excess chlorine is blown out of the mixture by means of nitrogen. The precipitated potassium chloride is filtered off and rinsed with approx. 200 ml of chlorobenzene. The filtrate is then distilled. When the sulfur dichloride and chlorobenzene have been distilled off, 171 g (91% of theory) of 2,6-dichlorobenzoxazole are obtained, having a melting point of 49°–51° C. and a boiling point of 124°–128.5° C. under approx. 25 mbars.

EXAMPLE 6 (COMPARISON)

202 g (1 mole) of 6-chloro-2-mercaptobenzthiazole and 3.5 g of dimethylformamide are suspended in 1,000 ml of tetrachloroethane, and 1.05 moles of chlorine are initially passed in at room temperature, followed by 1.4 moles of chlorine at 85° C. The sulfur dichloride and the tetrachloroethane are distilled off under normal pressure and 167.6 g of 2,6-dichlorobenzthiazole, corresponding to 82.1% of theory, are then obtained by vacuum distillation under a pressure of 1.3 mbars at a delivery temperature of approx. 123° C.

We claim:

1. In a process for the manufacture of 2,6-dichlorobenzthiazole or 2,6-dichlorobenzoxazole of the formula

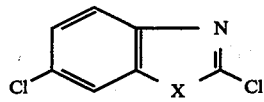

wherein X represents oxygen or sulfur, the improvement which comprises the step of chlorinating a potassium mercaptide salt of 6-chloro-3-mercaptobenzoxazole or of 6-chloro-2-mercaptobenzthiazole with chlorine in the presence of a halogenated aliphatic or halogenated aromatic hydrocarbon solvent, as a suspending means, said potassium mercaptide salt being substantially inert toward said solvent.

2. A process as claimed in claim 1, wherein the solvent used is chlorobenzene or o-dichlorobenzene.

3. A process as claimed in either of claims 1 or 2, wherein the chlorinating is carried out in the presence of catalytic quantities of an N-substituted carboxylic acid amide.

4. A process according to claim 1 or 2, wherein the reaction is carried out at an elevated temperature in the case of the thiazole.

5. A process according to claim 1, wherein the solvent used is carbon tetrachloride, tetrachloroethane, or a chlorinated benzene.

6. A process according to claim 1, wherein the chlorinating is carried out in the presence of 0.1 to 5% by weight, relative to the mercaptide salt, of dimethylformamide.

7. A process according to claim 1 comprising the steps of:
 (a) suspending the 6-chloro-2-mercaptobenzoxazole or 6-chloro-2-mercaptobenzthiazole sodium or potassium mercaptide salt in an inert halogenated aliphatic or aromatic organic solvent which does not substantially dissolve said sodium or potassium salt, thereby obtaining a suspension,
 (b) passing chlorine into said suspension to chlorinate said mercaptide salt, and
 (c) recovering the resulting 2,6-dichlorobenzthiazole or 2,6-dichlorobenzoxazole.

* * * * *